Figure 1:
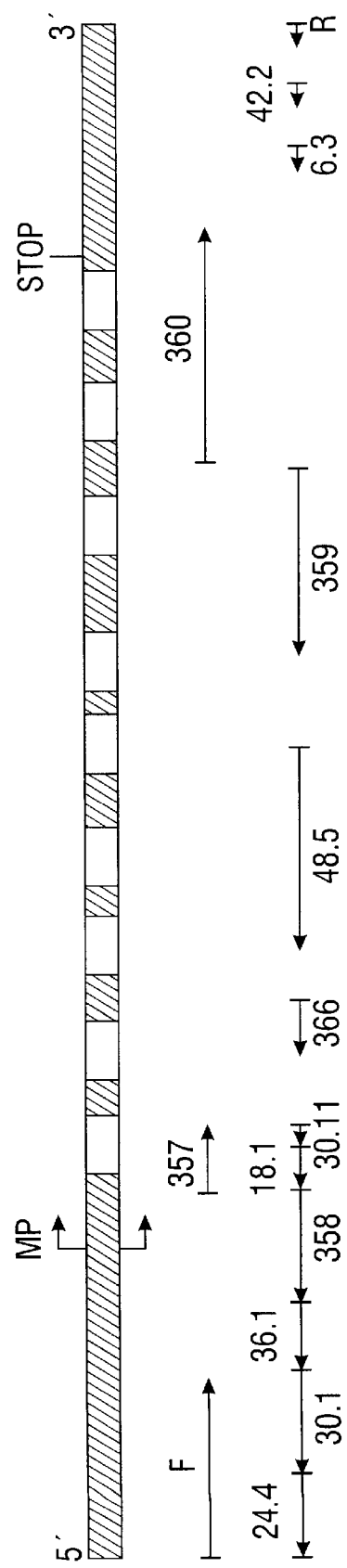

United States Patent [19]

Slabas et al.

[11] Patent Number: 6,011,201
[45] Date of Patent: Jan. 4, 2000

[54] β-KETOACYL ACP REDUCTASE GENES FROM *BRASSICA NAPUS*

[75] Inventors: Antoni Ryszard Slabas, Durham; Andrew White, Tyne & Wear; Dianne Chase, Cumbria; Keiran Elborough, Cleveland; Philip Anthony Fentem, Aberystwyth, all of United Kingdom

[73] Assignee: Zeneca Limited, London, United Kingdom

[21] Appl. No.: 08/793,035

[22] PCT Filed: Jul. 17, 1995

[86] PCT No.: PCT/GB95/01678

§ 371 Date: Jul. 28, 1997

§ 102(e) Date: Jul. 28, 1997

[87] PCT Pub. No.: WO96/02652

PCT Pub. Date: Feb. 1, 1996

[30] Foreign Application Priority Data

Jul. 20, 1994 [GB] United Kingdom .................... 9414622

[51] Int. Cl.[7] ................. A01H 5/00; C12N 15/82
[52] U.S. Cl. ................. 800/298; 435/320.1; 536/23.6
[58] Field of Search ............ 536/23.6; 435/320.1; 800/205, 298

[56] References Cited

U.S. PATENT DOCUMENTS 5,110,728  5/1992  Kridl et al. .................... 435/69.1

FOREIGN PATENT DOCUMENTS

| WO 92/14816 | 9/1992 | WIPO | C12N 9/02 |
| WO 92/18634 | 10/1992 | WIPO | C12N 15/82 |
| WO 95/07357 | 3/1995 | WIPO | C12N 15/82 |

OTHER PUBLICATIONS

Napoli et al. Introduction of a chimeric chalcone synthase gene into petunia results in reversible co–suppression of homologous genes in trans. The Plant Cell. 2:279–280, Apr. 1990.

Smith et al. Antisense RNA inhibition of polygalacturonase gene expression in transgenic tomatoes. Nature. 334:724–726, Aug. 1988.

Slabas et al. The biochemistry and molecular biology of plant lipid biosynthesis. Plant Molecular Biology. 19:169–191, May 1992.

Thomas, Neil C., et al., (1995) *Plant Lipid Metab.*, meeting date, Jun. 26–Jul. 1, 1994 11:99–101.

Martinez–Rivas, J.M., et al. (1993) *Grasas Y Aceites* 44;119–120.

Sheldon, P.S., et al. (1992) *Biochim Biophys Acta* 1120:151–159.

Klein, B., et al. (1992) *Molecular and General Genetics* 233:122–128.

Kapff, M., et al. (1993) *Biol. Chem. Hoppe–Seyler*, 374:528.

*Primary Examiner*—Elizabeth F. McElwain
*Attorney, Agent, or Firm*—Gary M. Bond; Arnold White & Durkee

[57] ABSTRACT

A full length cDNA of rape seed β-ketoreductase pJRS 10.1 having the Sequence ID-1.

8 Claims, 2 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1185 base pairs
        (B) TYPE: nucleic acid
        (C) STRANDEDNESS: single
        (D) TOPOLOGY: linear (xi) SEQUENCE DESCRIPTION: SEQ ID NO:1:

```
GGCACGAGCT TCCTTGGCCT CTCTCTCTCT CTCTCCCTCT CCACCCGTCT CCACCTCCTC      60

CTCCGTTCGA TGGCAACCAC CGTCGCAGCA ACAAAGCTCA CCTCCTTGAA AGCCGTCAAG     120

AAGCTCGGTT TCCGTGAGAT CCGTCAGGTC CGTCAATGGA CTCCGCTTCA GTCTTCGATG     180

CCTCATTTCG GATCGCGGCA GTCATTCGCA ACCTCCACTG TTGTGAAAGC TCAAGCGACA     240

GCTGTTGAGC AATCGACAGG AGAAGCTGTT CCGAAAGTGG AGTCTCCGGT GGTCGTTGTG     300

ACTGGTGCTT CGAGAGGGAT TGGTAAAGCT ATTGCTCTTT CCTTGGGCAA AGCTGGCTGC     360

AAGGTCTTGG TGAACTATGC TAGGTCAGCA AAGGAGGCTG AGGAAGTTTC TAAACAGATT     420

GAAGCATATG GAGGCCAGGC TATTACTTTT GGGGGTGATG TCTCCAAAGA GGCTGATGTG     480

GAAGCCATGA TGAAAACCGC TATTGATGCA TGGGGAACCA TTGATGTCGT CGTCAACAAT     540

GCAGGAATCA CTCGGGATAC CTTGTTGATA CGAATGAAGA AGTCCCAATG GGATGAAGTG     600

ATTGATTTGA ATCTCACTGG AGTCTTTCTC TGTACCCAGG CAGCAACAAA GATCATGATG     660

AAGAAGAGAA AGGGAAGAAT CATCAACATT GCGTCAGTTG TTGGTCTCAT TGGTAATATT     720

GGCCAAGCAA ACTACGCTGC TGCTAAAGCT GGTGTTATTG GGTTCTCCAA GACTGCCGCC     780

AGAGAGGGTG CGAGCAGGAA TATAAATGTC AATGTGGTTT GCCCTGGGTT CATTGCATCT     840

GACATGACTG CCAAGCTTGG AGAAGACATG GAAAAGAAAA TCTTGGGAAC AATCCCATTA     900

GGACGATATG GACAACCTGA AGATGTGGCT GGCTTGGTAG AATTCTTGGC TCTCAGTCCT     960

GCAGCTAGTT ACATCACAGG ACAGGCATTC ACCATTGATG GAGGTATTGC CATCTAGGCA    1020

TTTGTTAAGA GTTGCTTTGT GTTTAGGCAA AACCGATTTG GTAAAACAGA CAAAGTTGAG    1080

TTTATTCCGG CACTTGGTCG GATTTCTGTT CTGTGGATTC TGTTCGGAGA GAAATCTAAA    1140

ACGCATTGCT TAAACTAAGT TACGTAAAAA AAAAAAAAAA AAAAA                    1185
```

(2) INFORMATION FOR SEQ ID NO:2:

(i) SEQUENCE CHARACTERISTICS:
        (A) LENGTH: 1155 base pairs
        (B) TYPE: nucleic acid
        (C) STRANDEDNESS: single (D) TOPOLOGY: linear (xi) SEQUENCE DESCRIPTION: SEQ ID NO:2:

| | | | | | |
|---|---|---|---|---|---|
| CTCCTCCGTT | CGATGGCAAC | CACCGTCGCA | GCAACAAAGC | TCACCTCCTT GAAAGCCGTC | 60 |
| AAGAAGCTCG | GTTTCCGTGA | GATCCGTCAG | GTCCGTCAAT | GGACTCCGCT TCAGTCTTCG | 120 |
| ATGCCTCATT | TCGGATCGCG | GCAGTCATTC | GCAACCTCCA | CTGTTGTGAA AGCTCAAGCG | 180 |
| ACAGCTGTTG | AGCAATCGAC | AGGAGAAGCT | GTTCCGAAAG | TGGAGTCTCC GGTGGTCGTT | 240 |
| GTGACTGGTG | CTTCGAGAGG | GATTGGTAAA | GCTATTGCTC | TTTCCTTGGG CAAAGCTGGC | 300 |
| TGCAAGGTCT | TGGTGAACTA | TGCTAGGTCA | GCAAAGGAGG | CTGAGGAAGT TTCTAAACAG | 360 |
| ATTGAAGCAT | ATGGAGGCCA | GGCTATTACT | TTTGGGGGTG | ATGTCTCCAA AGAGGCTGAT | 420 |
| GTGGAAGCCA | TGATGAAAAC | CGCTATTGAT | GCATGGGGAA | CCATTGATGT CGTCGTCAAC | 480 |
| AATGCAGGAA | TCACTCGGGA | TACCTTGTTG | ATACGAATGA | AGAAGTCCCA ATGGGATGAA | 540 |
| GTGATTGATT | TGAATCTCAC | TGGAGTCTTT | CTCTGTACCC | AGGCAGCAAC AAAGATCATG | 600 |
| ATGAAGAAGA | GAAAGGGAAG | AATCATCAAC | ATTGCGTCAG | TTGTTGGTCT CATTGGTAAT | 660 |
| ATTGGCCAAG | CAAACTACGC | TGCTGCTAAA | GCTGGTGTTA | TTGGGTTCTC CAAGACTGCC | 720 |
| GCCAGAGAGG | GTGCGAGCAG | GAATATAAAT | GTCAATGTGG | TTTGCCCTGG GTTCATTGCA | 780 |
| TCTGACATGA | CTGCCAAGCT | TGGAGAAGAC | ATGGAAAAGA | AAATCTTGGG AACAATCCCA | 840 |
| TTAGGACGAT | ATGGACAACC | TGAAGATGTG | GCTGGCTTGG | TAGAATTCTT GGCTCTCAGT | 900 |
| CCTGCAGCTA | GTTACATCAC | AGGACAGGCA | TTCACCATTG | ATGGAGGTAT TGCCATCTAG | 960 |
| GCATTTGTTA | AGAGTTGCTT | TGTGTTTAGG | CAAAACCGAT | TTGGTAAAAC AGACAAAGTT | 1020 |
| GAGTTTATTC | CGGCACTTGG | TCGGATTTCT | GTTCTGTGGA | TTCTGTTCGG AGAGAAATCT | 1080 |
| AAAACGCATT | GCTTAAACTA | AGTTACGTAA | TATATGAACC | AAAGAGCTTT GTGGAAATGA | 1140 |
| TGGAAGCATG | TTTTG | | | | 1155 |

(2) INFORMATION FOR SEQ ID NO:3:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (xi) SEQUENCE DESCRIPTION: SEQ ID NO:3:

| | | | | | |
|---|---|---|---|---|---|
| TCGACTCACG | AGACTTTGAG | TATTTTGAGA | GTGACCAAGA | CGCAATGTAG TTGGTCTCGG | 60 |
| GTAGTTTGGT | TCTCACAAGC | TACTCCTAAA | TATGCATTCA | TGACTTGGTT GGCCTTATTG | 120 |
| AATAGGTTAT | CTACTATGGA | TAGAGTTGCA | AGATGGAGCC | AATGTGCGGA TACAATATGT | 180 |
| GTCCTCTGTA | AAACGGCTCA | AGAGACAAGA | GATCATCTCT | TTTTTGAGTG CTCTTATTCA | 240 |
| TCGCAGATAT | GGGGATCTCT | TGTAAAAGGG | ATATTGAAAG | AGACGTATAC AAACGAGTGG | 300 |
| AAGGACATTG | TGATTTGGAT | ATCTGATGAG | AAGATGGAAA | GGATGAGACT GTTTTGTATC | 360 |
| AGATATGCAT | TTCAAATAGC | ATTGTATACT | CTTTGGAGAG | AGAAACAA GGTTCGTCAT | 420 |
| GAGAAGAAGC | TCATGCCAAT | CGAAGTGCTG | AAGAAATTGG | TAGATAAAGG GGTGAGGAAT | 480 |
| AAGTTAAGTC | TGATGAGATC | AAAGAAAGTA | AGATTTATGG | AGAAAGGGTT ACAGTTTTGG | 540 |
| TTTAGTACAA | GATTGTAAAG | TTCTTTGAGT | TCTTATGGGG | AGTTACTAAA AAGATTACAT | 600 |
| AGTCTGCACC | ATTTGATGTA | AAAATGATCT | TTTTGGTGAA | TAACAATTTA ACATTCATTC | 660 |
| GGAAAAAAAA | AAAAAATAAT | AATAATCTTC | TCCGAATTGA | AATCGATTTG GTTTGGTTCG | 720 |
| GTTTAAGTCT | CTTTTATCTG | ACTAGTCCCA | CCAGTTCTCC | AACAATAAAA CTCAACTACA | 780 |

```
CAGACAACCT CGTTCGTATC GCTTTTCGAA TTTTTTTATT TATTTTCTCT TGAAATTATA      840

AAATACAAAA AGTCAAAGAC TTTTACTTAC TTTCGTCGCC TCTCTCTGAA TCGATCTTTT      900

CGGACGGAGT TTTCCATCTC CTCAACTCTC ACAGTTAAAC AACTGTGTCT CTATGTGTTC      960

GATGGCCACC ACCGTCGCAG CAACAAAACT CACCTCCTTG AAAGCCACCG CCGGGAAGCT     1020

CGGTTACCGT GAGATCTGCC AGGTCCGTCA ATGGTCTCCG CTTCAGTCTG CGATGCCTCA     1080

TTTCGGTATG CTGCGATGTA GACAGCCATT TGCAACCTCC ACTGGTAATT CAGCTTCTTT     1140

CTCTCGGGCT TGGCTGTTTC CCTTAAGACT CTCTCTCTCT CTCTTCTCAT TAGATTCTAT     1200

CTTCACGCAG TTGTGAACGC TCAAGCTCAA GCTCAAGCTC AAGCCACGGG TGTTGAGCAA     1260

ACAACGACAG AAGAAGAAGA AGCTGTTCCA AAAGTGGAA                            1299

(2) INFORMATION FOR SEQ ID NO:4:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO:4:

ATGGCCACCA CCGTCGCAGC AACAAAACTC ACCTCCTTGA AAGCCACCGC CGGGAAGCTC       60

GGTTACCGTG AGATCTGCCA GGTCCGTCAA TGGTCTCCGC TTCAGTCTGC GATGCCTCAT      120

TTCGGTATGC TGCGATGTAG ACAGCCATTT GCAACCTCCA CTGGTAATTC AGCTTCTTTC      180

TCTCGGGCTT GGCTGTTTCC CTTAAGACTC TCTCTCTCTC TCTTCTCATT AGATTCTATC      240

TTCACGCAGT TGTGAACGCT CAAGCTCAAG CTCAAGCTCA AGCCACGGGT GTTGAGCAAA      300

CAACGACAGA AGAAGAAGAA GCTGTTCCAA AAGTGGAA                              338

(2) INFORMATION FOR SEQ ID NO:5:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (xi) SEQUENCE DESCRIPTION: SEQ ID NO:5:

GGGCAAGCAA ACTACGCTGC AGCTAAAGCT GGAGTTATTG GGTTTTCCAA GACTGCCGCC       60

AGAGAGGGTG CTAGCAGGAA TATAAATGTA TGTAACCCAT ATACTCCTCT TTTTCATTCT      120

TTGGACAGGA TATTAAACTT GGTCCATTGA CCAATTTGCT CTTTTACAGG TGAACGTGGT      180

TTGCCCTGGA TTCATTGCAT CTGACATGAC TGCCAAGCTT GGAGAAGACA TGGAAAAGAA      240

AATCTTGGGA AATCTTGGGA ACAATCCCAT TAGGTTAAAA AAAAAATAGA GGGTTCAACT      300

TTTACATTGT GTTGTGGGTA GTTTTTCGTA GGTTAGGATG TATCTGATAC AAAGCAAACT      360

TGATTTTTTT TTTTCAGGAC GATATGGACA ACCAGAAGAT GTGGCTGGCT TGGTC           415

(2) INFORMATION FOR SEQ ID NO:6:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (xi) SEQUENCE DESCRIPTION: SEQ ID NO:6:

CGCCAAACCA TGATAAAAAG TGCCACTCCA GCGATATGTG GCTAAACAAA AAGTGTCCTA       60
```

```
AATGGTAAGA CACTCATTGA TAAATAACAT ATTGGTTTGA TGTTGGGTAT ATACAGGTTC       120

GGTATAAAAT TGGTTCGGTT CAATCTGTTT GACTTCCAGC TTGCTGTCTA AATTCAACTA       180

CTACTGCAGT GGGCACACAC AAACCTTGTT CGTATCGCTG CTTTTCGAAA ATTTCTCATT       240

TAAATATATA TATATATATT TTTTTTTTCA TTTAAATATT TGTTTAGAGA AGAAAGACAA       300

GATTACGACT TTTTCTTCCT TCCCATCTCT CTCCTCTTCA AGGATTCGAT CTTTACGAGG       360

TTCGCTAGTA CAGACGGCTT TTCTCTGATC TCCACTCTCG CCGTTAAACA ACCCATTCTC       420

CGTTCCATGG CCACCACCTC CATCGCAGGA CCCAGACTCA CTTCCTTGAA AACCGCCGCC       480

GGGAAGCTCG GCTACCGTGA GATCTGTCAT GTCCGGCAAT GGGCTCCGGT TCATTCTCCG       540

ATGCCTCATT TCGGAATGCT GCGATGTGGA TCGCGACGCC CGTTTGCAAC CTCCTCCTCC       600

ACTGGTATTC AGCTCCCCTC TCTCTCTCTG TTCCCTTAAC ATTTCGATCA TCTCCATTCT       660

CATTAGAAGA TTCTATCCTA TCAGTTGTTC AAGCTCAAGC TCAAGCCACT GCTGCTGAGC       720

AATCAACAGG TGAAGAAGAA GCTGGTCCGA AAGTGGAG                               758

(2) INFORMATION FOR SEQ ID NO:7:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO:7:

ATGGCCACCA CCTCCATCGC AGGACCCAGA CTCACTTCCT TGAAAACCGC CGCCGGGAAG        60

CTCGGCTACC GTGAGATCTG TCATGTCCGG CAATGGGCTC CGGTTCATTC TCCGATGCCT       120

CATTTCGGAA TGCTGCGATG TGGATCGCGA CGCCCGTTTG CAACCTCCTC CTCCACTGGT       180

ATTCAGCTCC CCTCTCTCTC TCTGTTCCCT TAACATTTCG ATCATCTCCA TTCTCATTAG       240

AAGATTCTAT CCTATCAGTT GTTCAAGCTC AAGCTCAAGC CACTGCTGCT GAGCAATCAA       300

CAGGTGAAGA AGAAGCTGGT CCGAAAGTGG AG                                    332

(2) INFORMATION FOR SEQ ID NO:8:

(i) SEQUENCE CHARACTERISTICS:
        (A) LENGTH: 408 base pairs
        (B) TYPE: nucleic acid
        (C) STRANDEDNESS: single
        (D) TOPOLOGY: linear (xi) SEQUENCE DESCRIPTION: SEQ ID NO:8:

GGCCAAGCAA ACTACGCTGC TGCTAAAGCT GGAGTTATCG GGTTCTCCAA GACTGCTGCC        60

AGAGAGGGTG CGAGCAGGAA TATTAACGTA CGCGACCTAG CTTCTCTCTT TCTTTCCTTG       120

GAGGCTTGCT TGTACAAGAT TTTTAAGTTG GTCTGGTCTG TTAACGGTTT TCTCTATTAC       180

AGGTCAATGT GGTTTGCCCC GGGTTCATTG CATCTGACAT GACTGCTAAA CTTGGAGAAG       240

ACATGGAAAA GAAATCTTG GAACAATCC CATTAGGTAA TGGAGAGTCA AGATTTTACA        300

TTTGTTGCGG TTATTTTATG TAGGTTATTA GTATGTCTCT GATACAAAGC AAACTGGATT       360

AATTTTTCAG GACCATATGG ACAACCGGAA GATGTGGCTG GCTTGGTA                   408

(2) INFORMATION FOR SEQ ID NO:9:

(i) SEQUENCE CHARACTERISTICS:
        (A) LENGTH: 315 amino acids
        (B) TYPE: amino acid
        (C) STRANDEDNESS: single
        (D) TOPOLOGY: linear
```

(xi) SEQUENCE DESCRIPTION: SEQ ID NO:9:

```
Met Ala Thr Thr Val Ala Ala Thr Lys Leu Thr Ser Leu Lys Ala Val
1               5                   10                  15

Lys Lys Leu Gly Phe Arg Glu Ile Arg Gln Val Arg Gln Trp Thr Pro
                20                  25                  30

Leu Gln Ser Ser Met Pro His Phe Gly Ser Arg Gln Ser Phe Ala Thr
            35                  40                  45

Ser Thr Val Val Lys Ala Gln Ala Thr Ala Val Glu Gln Ser Thr Gly
        50                  55                  60

Glu Ala Val Pro Lys Val Glu Ser Pro Val Val Val Thr Gly Ala
65                  70                  75                  80

Ser Arg Gly Ile Gly Lys Ala Ile Ala Leu Ser Leu Gly Lys Ala Gly
                85                  90                  95

Cys Lys Val Leu Val Asn Tyr Ala Arg Ser Ala Lys Glu Ala Glu Glu
                100                 105                 110

Val Ser Lys Gln Ile Glu Ala Tyr Gly Gly Gln Ala Ile Thr Phe Gly
            115                 120                 125

Gly Asp Val Ser Lys Glu Ala Asp Val Glu Ala Met Met Lys Thr Ala
        130                 135                 140

Ile Asp Ala Trp Gly Thr Ile Asp Val Val Asn Asn Ala Gly Ile
145                 150                 155                 160

Thr Arg Asp Thr Leu Leu Ile Arg Met Lys Lys Ser Gln Trp Asp Glu
                165                 170                 175

Val Ile Asp Leu Asn Leu Thr Gly Val Phe Leu Cys Thr Gln Ala Ala
            180                 185                 190

Thr Lys Ile Met Met Lys Lys Arg Lys Gly Arg Ile Ile Asn Ile Ala
        195                 200                 205

Ser Val Val Gly Leu Ile Gly Asn Ile Gly Gln Ala Asn Tyr Ala Ala
    210                 215                 220

Ala Lys Ala Gly Val Ile Gly Phe Ser Lys Thr Ala Ala Arg Glu Gly
225                 230                 235                 240

Ala Ser Arg Asn Ile Asn Val Asn Val Val Cys Pro Gly Phe Ile Ala
                245                 250                 255

Ser Asp Met Thr Ala Lys Leu Gly Glu Asp Met Glu Lys Lys Ile Leu
                260                 265                 270

Gly Thr Ile Pro Leu Gly Arg Tyr Gly Gln Pro Glu Asp Val Ala Gly
            275                 280                 285

Leu Val Glu Phe Leu Ala Leu Ser Pro Ala Ala Ser Tyr Ile Thr Gly
        290                 295                 300

Gln Ala Phe Thr Ile Asp Gly Gly Ile Ala Ile
305                 310                 315
```

(2) INFORMATION FOR SEQ ID NO:10:

(i) SEQUENCE CHARACTERISTICS:
        (A) LENGTH: 315 amino acids
        (B) TYPE: amino acid
        (C) STRANDEDNESS: single
        (D) TOPOLOGY: linear (xi) SEQUENCE DESCRIPTION: SEQ ID NO:10:

```
Met Ala Thr Thr Val Ala Ala Thr Lys Leu Thr Ser Leu Lys Ala Val
1               5                   10                  15

Lys Lys Leu Gly Phe Arg Glu Ile Arg Gln Val Arg Gln Trp Thr Pro
                20                  25                  30
```

```
Leu Gln Ser Ser Met Pro His Phe Gly Ser Arg Gln Ser Phe Ala Thr
    35                  40                  45

Ser Thr Val Val Lys Ala Gln Ala Thr Ala Val Glu Gln Ser Thr Gly
    50                  55                  60

Glu Ala Val Pro Lys Val Glu Ser Pro Val Val Val Thr Gly Ala
65              70                  75                  80

Ser Arg Gly Ile Gly Lys Ala Ile Ala Leu Ser Leu Gly Lys Ala Gly
            85                  90                  95

Cys Lys Val Leu Val Asn Tyr Ala Arg Ser Ala Lys Glu Ala Glu Glu
            100                 105                 110

Val Ser Lys Gln Ile Glu Ala Tyr Gly Gly Gln Ala Ile Thr Phe Gly
        115                 120                 125

Gly Asp Val Ser Lys Glu Ala Asp Val Glu Ala Met Met Lys Thr Ala
        130                 135                 140

Ile Asp Ala Trp Gly Thr Ile Asp Val Val Val Asn Asn Ala Gly Ile
145                 150                 155                 160

Thr Arg Asp Thr Leu Leu Ile Arg Met Lys Lys Ser Gln Trp Asp Glu
            165                 170                 175

Val Ile Asp Leu Asn Leu Thr Gly Val Phe Leu Cys Thr Gln Ala Ala
            180                 185                 190

Thr Lys Ile Met Met Lys Lys Arg Lys Gly Arg Ile Ile Asn Ile Ala
        195                 200                 205

Ser Val Val Gly Leu Ile Gly Asn Ile Gly Gln Ala Asn Tyr Ala Ala
    210                 215                 220

Ala Lys Ala Gly Val Ile Gly Phe Ser Lys Thr Ala Ala Arg Glu Gly
225                 230                 235                 240

Ala Ser Arg Asn Ile Asn Val Asn Val Val Cys Pro Gly Phe Ile Ala
            245                 250                 255

Ser Asp Met Thr Ala Lys Leu Gly Glu Asp Met Glu Lys Lys Ile Leu
            260                 265                 270

Gly Thr Ile Pro Leu Gly Arg Tyr Gly Gln Pro Glu Asp Val Ala Gly
        275                 280                 285

Leu Val Glu Phe Leu Ala Leu Ser Pro Ala Ala Ser Tyr Ile Thr Gly
    290                 295                 300

Gln Ala Phe Thr Ile Asp Gly Gly Ile Ala Ile
305                 310                 315
```

β-KETOACYL ACP REDUCTASE GENES FROM *BRASSICA NAPUS*

This invention relates to the β-ketoacyl ACP reductase genes from *Brassica napus* and uses thereof.

The overall pathway of fatty acid synthesis from malonyl CoA is the same in all organisms. However the structural organisation of the participating enzymes varies widely among different kingdoms. A single multifunctional fatty acid synthase (FAS) polypeptide is found in mammals, whereas two interacting multifunctional polypeptides function in yeast. In contrast, in prokaryotes and plants each step in the FAS pathway is catalysed by a separate monofunctional enzyme. The enzyme activities which make up this pathway include "condensing enzymes" which catalyse the reaction of malonyl ACP with an acyl ACP (or acetyl CoA in the case of KASIII which initiates the pathway) producing a β-ketoacyl ACP (with a chain length 2 carbon atoms longer than the initial acceptor). These molecules are then reduced by β-ketoacyl ACP reductase to a β-hydroxyacyl ACP. A dehydratase enzyme then converts this intermediate to an enoyl ACP which is subsequently reduced by enoyl reductase to generate a fatty acyl ACP. In plants evidence from cellular fractionation and immunolocalisation studies suggests that fatty acid synthesis takes place in plastids. In leaves these are chloroplasts, in seeds these are leucoplasts.

This invention is principally concerned with genes encoding the FAS pathway enzyme NADPH linked β-ketoacyl ACP reductase (β-ketoreductase). Two forms of this enzyme, one NADPH-linked, the other NADH-linked, have been reported to be localised in plastids. The function of the NADH-linked enzyme is unknown. It is the NADPH-linked enzyme that functions in fatty acid biosynthesis. This NADPH-linked β-ketoreductase is coordinately induced with other fatty acid biosynthetic enzymes, just before and during lipid accumulation in developing oil seeds.

Partial length cDNA clones encoding β-ketoreductase, of chain length 0.32 kb and 0.1 kb have already been isolated from a cDNA library from developing seed of *Brassica napus*, and a full length cDNA within a 1.2 kb clone has already been isolated from a cDNA library from Arabidopsis leaf (Slabas et al (1992)).

An object of this invention is to provide gene sequences encoding β-ketoacyl ACP reductase.

According to the present invention there are provided:
(a) a full length cDNA of rape seed β-ketoreductase pJRS10.1
(b) a full length cDNA of rape leaf β-ketoreductase pJRL6.2
(c) genomic DNAs of rape β-ketoreductase: pJGR11.7, pJGR24.10, pJGR27.11.

The cDNA of rape seed β-ketoreductase, according to the invention, may be used as a heterologous probe to select clones of β-ketoreductase genes from other oilseeds eg soya, sunflower, maize, coconut, oil palm.

Also, the genomic DNA of rape seed β-ketoreductase may be used to recover the promoter of this gene. This promoter can be used to generate RNA in a tissue specific and developmentally regulated way. The RNA so generated may promote expression of β-ketoreductase or may encode another protein, for example another enzyme, which will then be expressed specifically in the developing oilseed.

Additionally, the cDNAs of rape seed ketoreductase can be used to make expression cassettes (sense or antisense) to transform rape to down regulate production of the seed β-ketoreductase enzyme. This will produce rape plants with low or modified oil content. Down-regulation will divert metabolism of assimilates into alternative storage compounds eg starch, protein or other polymers inserted by genetic engineering, such as PHB.

Further according to the invention full length cDNAs of rape β-ketoreductase can be used to create expression cassettes either with a powerful promoter, or by inserting extra copies of the gene, to promote over-expression of β-ketoreductase, leading to rape plants with enhanced oil content.

The full length cDNAs of rape seed and leaf ketoreductase genes contain "transit peptide" sequences which direct the ketoreductase proteins to chloroplasts or leucoplasts, the transit peptide being cleaved of during import of the protein into the plastid. These transit peptides can therefore be used in gene fusions to direct other proteins to the plastids of leaf and seed tissues.

We have prepared a poly dT primed cDNA library from developing rape embryo and have obtained another from rape leaf. A full length Arabidopsis cDNA clone was already available. A 0.2 kb fragment corresponding to the 5' part of the mature protein of the Arabidopsis cDNA clone was used as a probe to screen the rape embryo cDNA library. A full length 1.2 kb cDNA clone (pJRS10.1) was thereby isolated and sequenced. This contained an open reading frame corresponding to 315 amino acids.

The rape leaf cDNA library was probed with a 0.96 kb fragment from the Arabidopsis leaf β-ketoreductase cDNA. A 1.2 kb cDNA clone (pJRL6.2) was thereby isolated and sequenced. This was found to contain the full open reading frame of the β-ketoreductase gene.

A 0.32 kb rape seed cDNA fragment which was already available (Slabas et al (1992)) was used to probe a rape embryo genomic DNA library. Nine classes of genomic DNA clones were identified by restriction analysis and clones corresponding to these classes were subcloned into a plasmid vector. Partial sequence analysis showed that 5 classes were present. Four subclones—pJGR3.2, pJGR11.7, pJGR24.10 and pJGR27.11—were subject to further sequence analysis.

Two genomic clones were isolated from an Arabidopsis genomic library using exactly the same screening procedure, but the 0.96 kb fragment from Arabidopsis cDNA was used as a probe rather than the rape cDNA. These genomic clones showed differences in the 5' transit peptide sequence, at the nucleotide and amino acid level.

The rape leaf and seed cDNAs showed no difference in the 5' transit peptide sequence at either the nucleotide or amino acid level. They did, however, show small differences in the 3' untranslated region. The genomic clone 27.11 shows significant homology to the seeds cDNA 6.1.

Seed specific expression of the gene corresponding to one of the β-ketoreductase genomic clones was found by single strand confirmation poltmorphisms and statistical analysis of cDNAs isolated.

The promotor of the putative seed expressed reductase gene was used in a GUS gene fusion cassette. Expression of this gene in transgenic rape plants showed the expression of the GUS gene was seed specific.

The following clones have been deposited, in *Escherichia coli* strain XL1-Blue, with the National Collection of Industrial and Marine Bacteria Limited, 23 St.Machar Drive, Aberdeen AB2 1RY, under the terms of the Budapest Treaty on the Deposit of Microorganisms for Patent Purposes:

| Clone Name | Date of Deposit | Accession Number |
| --- | --- | --- |
| pJGR11.7 | May 26th, 1994 | NCIMB 40640 |
| pJGR24.10 | May 26th, 1994 | NCIMB 40641 |
| pJGR27.11 | May 26th, 1994 | NCIMB 40642 |

Confirmatory evidence that the clones encode ketoreductase is that:

The rape seed cDNA pJRS10.1 and the rape leaf cDNA pJRL6.2 showed substantial sequence homology at both the nucleotide and amino acid level with the Arabidopsis β-ketoreductase cDNA previously isolated.

Antibodies raised against avocado β-ketoreductase strongly recognise the protein produced by expression of the open reading frame of clone pJRS10.1 in *E.coli*.

Crude extracts of *E.coli* expressing the open reading frame of the clone pJRS10.1 showed β-ketoreductase enzyme activity markedly enhanced over that of non-transformed *E.coli*.

The invention will now be described in detail with reference to the following Figures where:

FIG. 1 shows a map corresponding to Arabidopsis genomic clone pJGA19.3. The introns are shown in white and the exons in black. The map is not drawn to scale. The regions for which sequence has been obtained are indicated.

Figure 2:
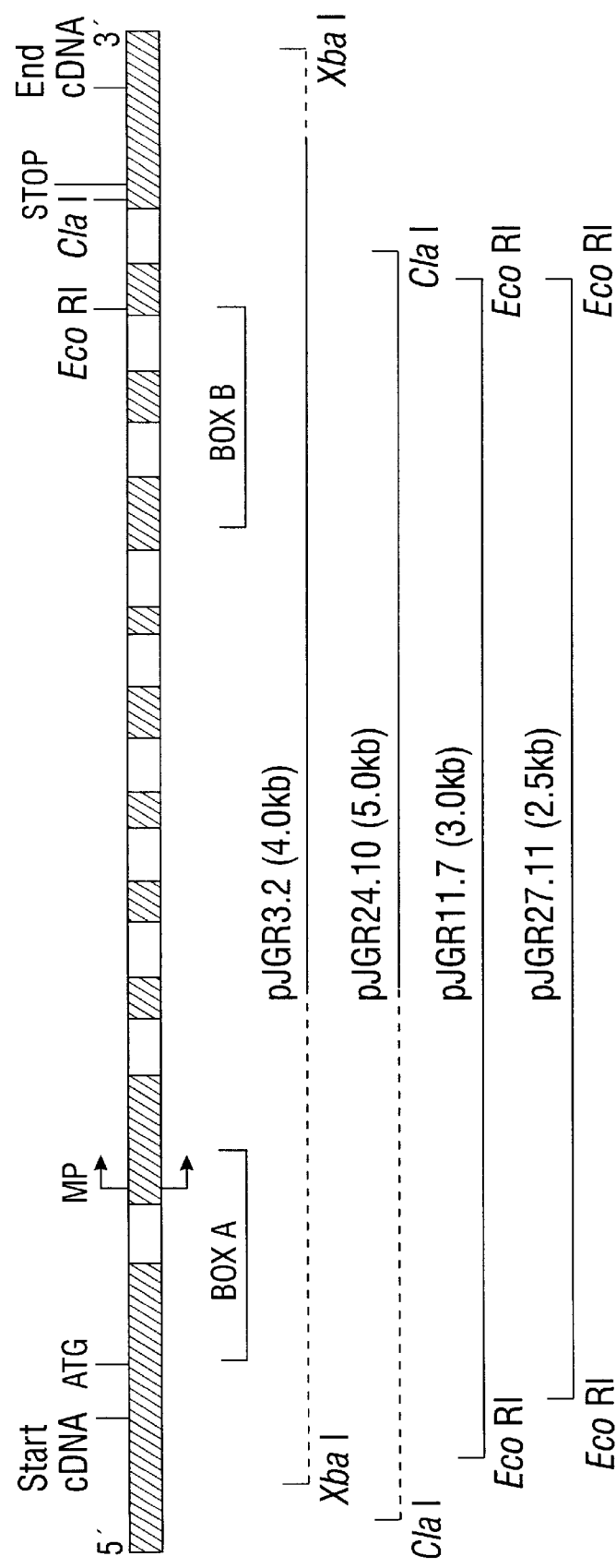

FIG. 2 shows a theoretical map corresponding to the rape β-ketoreductase genomic subclones. The introns are shown in white and the exons in black. The introns are not drawn to scale. A dashed line indicates a cloning artefact. The positions of Box A and Box B, which have been sequenced in both directions, are shown.

The following nucleotide sequences are provided herewith:

Sequence ID-1 is the nucleotide sequence of the rape seed cDNA clone pJRS10.1.

Sequence ID-2 is the nucleotide sequence of the rape leaf cDNA clone pJRL6.2.

Sequence ID-3 is the nucleotide sequence of rape genomic subclone pJGR11.7 5' region Sequence ID-4 is the nucleotide sequence of rape genomic subclone pJGR 11.7 Box A.

Sequence ID-5 is the nucleotide sequence of rape genomic subclone pJGR 11.7 Box B.

Sequence ID-6 is the nucleotide sequence of rape genomic subclone pJGR 27.11 5' region.

Sequence ID-7 is the nucleotide sequence of rape genomic subclone pJGR2 7.11 Box A.

Sequence ID-8 is the nucleotide sequence of rape genomic subclone pJGR27.11 Box B.

Sequence ID-9 is the amino acid sequence encoded by the open reading frame in Sequence ID-1 from nucleotide position 70 to nucleotide position 1017.

Sequence ID-10 is the amino acid sequence encoded by the open reading frame in Sequence ID-2 from nucleotide position 13 to nucleotide position 960.

The invention will now be described in the following Example.

EXAMPLE

Materials and Methods 1.1 Preparation of Competent XL1 Blue and 0359 *Escherichia coli* Cells XL1 Blue cells were grown overnight in 50 ml LB media+0.2% maltose+50 ml tetracycline. Q359 cells were grown without the addition of tetracycline. The cells were centrifuged at 3000 g for 10 mins and the cell pellet taken up in 5 ml 10 mM $MgSO_4$ and stored at 4° C. Cells were used fresh for primary screening and no older than two days for subsequent screening.

1.2 Rape Seed cDNA Library

The cDNA library used was generated using the mRNA from mid stage developing Jet neuf rape embryos (harvested at approximately 7–8 weeks days post anthesis). The 1 strand synthesis was carried out according to the manufacturer's instructions (Amersham International). The resulting cDNA generated was cloned into the Eco RI/Xho site of l-ZAP as recommended by the manufacturers (Stratagene). The host bacteria used was XL1 Blue (see paragraph 1.1 for preparation of cells).

1.3 Rape Genomic Library

The rape genomic library used was derived from Jet neuf total DNA. After Sau 3A partial digest, it was cloned in EMBL 3A. The host bacteria used was Q359 (see paragraph 1.1 for preparation of cells).

1.4 Probe Preparation and Labelling

Plasmid DNA from Arabidopsis β-ketoreductase 1.2 kb cDNA clone and rape β-ketoreductase 0.32 kb cDNA clone (5) was prepared by the Qiagen tip method as recommended by the manufacturers (Qiagen inc.). Probe for the screening of rape seed cDNA library was generated by a Xho 1/Hpa (20 U each) double digest of 10 μg of the plasmid containing the Arabidopsis cDNA clone (1.2 kb) to give an isolated fragment size of 0.2 kb. Probe for the screening of rape genomic library was generated by the digestion of 1 μg of the plasmid containing the rape cDNA clone (0.32 kb) with 20 U Eco RI, and the fragment isolated was 0.32 kb. All digests were carried out using restriction enzymes from Boehringer at 37° C. for 3.4 h. Digest were separated by 1% TAE buffered agarose gel electrophoresis and the required fragments cut out from the gel. The DNA was obtained from the gel slice using the method recommended by Geneclean II (Bio 101). DNA concentration was determined by spectrophotometry.

The probes (200–300 ng) were radio-labelled with α-$^{32}$PdCTP using the Megaprime kit from Amersham International to a level of $5 \times 10^9$ dpm/μg. Unincorporated label was removed using Bio-Spin chromatography columns (Bio-Rad).

Just before use for hybridisation the radio-labelled probe was boiled for 5 min. and place on iced water for 2 min. before being added to hybridisation buffer at 65° C.

1.5 cDNA Library Primary Screening

For the rape seed cDNA library 4×50,000 pfu's (200,000 total pfu's) were added to 2 ml of competent XL1 blue cells, mixed and incubated at 37° C. for 20 min. The cultures were then added to 4×30 ml top agarose which had been melted and held at 55° C., mixed briefly and poured onto prewarmed (37° C.) 4 large LB plates (243×243×18 mm). Plates were left at room temperature for 20 min and incubated overnight at 37° C. The plates were finally incubated at 4° C. for 30 min.

Square sheets of nitrocellulose were carefully placed onto the surface of each plate and allowed to soak in for 2 min., pealed off and placed onto 3MM blotting paper soaked in denaturing solution (1.5 M NaCl. 0.5 M NaOH) for 2 min. To neutralise the filters each was subsequently placed for 2 min. onto 3MM paper soaked in neutralising solution (1.5 M NaCl, 0.5 M Tris-HCl pH 7.4) and finally for 2 min. onto 3MM paper soaked in 2× SSC. To immobilise the blotted DNA each filter was placed in a vacuum oven at 80° C. for 1 h.

The filters were incubated in 20 ml pre-hybridisation buffer (6× SSC, 1× Denhardt's 0.5% SDS, 0.05% Sodium Pyrophosphate, 50 g/ml Herring sperm DNA) with constant mixing for 2 h. at 65° C. at which point the buffer was discarded. The radio-labelled probe (see paragraph 1.4) was added to 10 ml hybridisation buffer (6× SSC, 1× Denhardt's, 0.5% SDS, 0.05% Sodium Pyrophosphate, 1 mM EDTA) previously equilibrated to 65° C. and hybridisation buffer/probe removed but retained at −20° C. for the subsequent screens To wash off the unbound probe the filters were washed with 1× SSC, 0.1% SDS for 30 min. at room temperature and then the same solution for 2×30 min. at 65° C. Filters were air dried and exposed to film overnight at −80° C. Positive plaques were located and pulled out from the plate using the wide end of a Pasteur pipette. The plug was placed into a microcentrifuge tube containing 1 ml SM buffer and 10 μl chloroform, vortexed and incubated at room temperature for 1 h. The suspension was spun for 2 min. on a bench top centrifuge and 750 μl of the supernatant containing the pfu's retained was removed and kept at 4° C.

1.6 Genomic Library Primary Screening

For the rape genomic library 4×50,000 pfu's (200,000 total pfu's) were screened using competent Q359 cells on 4 plates. The methods used were as already described (see paragraph 1.5) but in a genetic manipulation isolation unit.

1.7 cDNA and Genomic Secondary Screening

50–200 pfu's in 100 μl SM buffer were added to 50 μl of competent cells, mixed and incubated at 37° C. for 20 min. The culture was then added to 3 ml melted top agarose at 55° C., mixed briefly and poured onto pre-warmed (37° C.) small LB plates (850 mm diameter). Plates were held at room temperature for 20 min, and incubated overnight at 37° C. The plates were finally incubated at 4° C. for 30 min.

Pre-hybridisation and hybridisation were carried out in the same way as that in the primary screen (see paragraph 1.5), using the same hybridisation buffer/probe boiled for 5 min before use.

The procedure for lifting, preparing, probing, washing and exposing the filters was essentially the same as that already described (see paragraph 1.5).

The positive plaques were removed as a plug using the narrow end of a Pasteur pipette, placed into microcentrifuge tubes containing 500 μl SM buffer and 10 μl chloroform vortexed and incubated at room temperature for 1 h. The suspension was spun for 2 min. in a bench top centrifuge and 450 μl of the supernatant containing the pfu's retained was removed and kept at 4° C.

1.8 cDNA and Genomic Tertiary Screening

The method was essentially the same as that for the secondary screen (see paragraph 1.7) using only 10–20 pfu's per plate. Exposure of the nitrocellulose filters was only required for 4 h at room temperature in this instance.

1.9 Isolation of DNA from Positive Plaques

Plasmid rescue for cDNA clones was carried out as described by the Stratagene protocol for "In vivo excision of pSK from l-ZAP II clones". The DNA from the pSK derived clones was prepared in large quantities using the Qiagen tip method.

1.10 Preparation of Genomic DNA from Positive Plaques

20 μl of phage supernatant obtained after the tertiary screen was incubated with 500 μl fresh competent KW251 cells (see paragraph 1.1) at 37° C. for 20 min. This culture was added to 50 ml pre-warmed LB media (37° C. for 5–7 h. After that 250 μl chloroform was added to the culture and incubated for a further 15 min. at 37° C. Cell debris was spun out at 10,000×g at room temperature for 10 min and DNase/RNase added to the supernatant to a final concentration of 1 μg/ml and incubated at 37° C. for 30 min. 5 g Polyethylene glycol 8000 and 3.2 g NaCl was added, dissolved gently with magnetic stirrer and the solution was incubated at 4° C. overnight.

The resultant suspension was centrifuged at 10,000×g at 4° C. for 20 min., and the phage particles taken up in 5 ml 20 mM Tris-Hcl pH 7.4, 100 mM $MgSO_4$. The solution was extracted twice with chloroform, and twice with phenol:chloroform (1:1). To precipitate the DNA, an equal volume of cold isopropanol was added and left on ice for 30 min. The precipitated DNA was centrifuged at 10,000×g and washed with cold 70% ether before being pelleted again. The DNA was resuspended in 200 μl of 10 mM Tris-HCl pH7.5, 1 mM EDTA.

1.11 Sequencing DNA Clones

Sequencing was carried out by the manufacturer's recommended methods for the machine used (Applied Biosystems Inc. 373A DNA sequencer). Both forward and reverse primers (−21m13 and M13RP1) were used initially for all clones. Oligonucleotides generated from the Arabidopsis cDNA clone (1.2 kb) were used to further sequence pJRS10.1 (rape seed cDNA clone); pJGR3.2: pJGR11.7; pJGR24.10 and pJGR27.11 (Rape genomic clone pJRS10.1; pJGR3.2; pJGR11.7 and pJGR24.10 were subjected to nested deletions by the recommended method (Pharmacia, "d.s. Nested Deletion Kit") and sequenced with forward and reverse primers and generated oligonucleotide priming. Computer analysis of DNA sequence was carried out using the SEQNET package from the SERC facility at Daresbury and DNA Strider.

1.12 Overexpression Studies

Oligonucleotides were synthesized in order to amplify by PCR the sequence encoding the mature protein, thus creating restriction sites for Bam Hl and Nco 1 at the termini. This PCR fragment was inserted into Bam Hl/Nco 1 digested pET-11d vector and transformed into *E.coli* BL21 (DE3) for expression of β-ketoreductase.

1.13 Molecular Techniques

Southern blots, northern blots, polymerase chain reaction and subcloning were carried out according to the methods used by Sambrook et al.

1.14 β-ketoreductase Enzyme Assay

β-ketoreductase activity was monitored by measuring the decrease of $A_{340}$ according to the protocol of Slabas et al.

Results and Discussion cDNA Cloning

A 0.2 kb fragment corresponding to the 5 part of the mature protein of the *Arabidopsis thaliana* β-ketoreductase cDNA clone was used as a probe to screen a l-ZAP rape seed cDNA library. Several clones were isolated and the largest was chosen for DNA sequencing.

This 1.2 kb rape embryo β-ketoreductase cDNA clone, inserted between the Eco Rl and Xho 1 site of the multicloning cassette of pSK, was called pJRS10.1. The DNA was recovered by plasmid rescue in the host *E.coli* strain XL1 Blue.

The nucleotide sequence of the rape seed cDNA clone (SEQ.ID-1) contains an ORF of 945 bp corresponding to a polypeptide of 315 amino acids. The 3' untranslated region is 171 bp in length including a polyadenylated tail. At the 5' end of the clone there is an untranslated region of 69 bp. The degree of identity between the encoded proteins of the rape seed and Arabidopsis leaf cDNA clones was extremely high at the nucleotide and amino acid level. Comparison of both sequences reveals that the rape seed protein is synthesized as a precursor containing an N-terminal extension of 55-amino acids. The 55-amino acid extension shows the three distinct features characteristic of stromal-targetting plastid transit peptides.

A 0.96 kb fragment from the Arabidopsis leaf β-ketoreductase cDNA was used as a probe to screen a cDNA library from rape leaf.

Two clones were isolated, inserted in the Eco R1 site of the multicloning cassette of pSK—pJRL6.2 (1.2 kb) and pJRL7.1 (2.4 kb). The DNA was recovered by plasmid rescue in the host strain XL 1 Blue. Both these clones were sequenced. pJRL6.2 was found to contain the full open reading frame of the β-keto-reductase gene (SEQ. ID-2). Clone pJRL7.1 had identical sequence at the 3' end but obviously contained a cloning artefact at its 5' end.

Southern and Northern Analysis

Using the rape seed cDNA clone as a probe in Southern blot hybridization experiments with restricted rape DNA, several hybridizing bands were observed. The results shown in FIG. 1 suggest that β-ketoreductase in rape is encoded by a small gene family of 3 members. Northern blot analysis was performed using mRNA isolated from rape leaves and seeds and using pJRS10.1 as probe. As shown in FIG. 2, an RNA band of 1.7 kb was detected but with different intensity in both tissues showing that the expression of this gene in seeds is approximately 20 times higher than in leaves.

Overexpressed Protein

The rape seed β-ketoreductase cDNA clone was overexpressed in a E.coli expression vector for the production of large quantities of protein. The quantification of the level of expression by SDS-PAGE showed that 5% of total soluble protein corresponded to β-ketoreductase. Antibodies raised against avocado β-ketoreductase are non-cross reactive with the rape protein but strongly recognise the overproduced rape enzyme in E.coli probably as a result of a higher concentration of the rape protein. To check if the overexpressed enzyme is biologically active, crude extracts from E.coli BL21 (DE3) induced with IPTG transformants were obtained and assayed for β-ketoreductase. High levels of activity compared with non-transformants were observed.

Arabidopsis β-ketoreductase Genomic Clones

Five independent genomic clones were isolated in l-FIX ll vector, which strongly hybridized to a 0.96 kb fragment of the Arabidopsis cDNA used as a probe. These were called as follows: lJA15; lJA16; lJA17; lJA19; lJA22

Restriction digests showed that broadly 3 classes were present:

Class 1=lJA19; lJA15

Class 2=lJA22; lJA16

Class 3=lJA17 (appears to be an overlapping clone of lJA22)

Clones corresponding to the classes 1 and 2 were subcloned into plasmid vector pSK as follows:

Clone lJA19: A Hind lll fragment of 4.0 kb was cloned into the Hind lll site of pSK giving pJGA19.3.

Clone lJA22: A Hind lll fragment of 5.0 kb was cloned into the Hind lll site of pSK giving pJGA22.4.

The host strain for these subclones was *Escherichia coli* XL1 blue. Both pJGA 19.3 and pJGA 22.4 have been partially sequenced.

FIG. 3 shows a map corresponding to subclone pJGA 19.3, with the areas indicated for which sequence has been obtained.

Rape β-ketoreductase Genomic Clones 35 independent genomic clones were isolated from the EMBL 3A library. These were termed:

lJR1; lJR2; lJR3; lJR4; lJR5; lJR6; lJR7; lJR8; lJR10; lJR11; lJR12; lJR14; lJR15; lJR16; lJR19; lJR20; lJR21; lJR22; lJR23; lJR24; lJR25; lJR26; lJR27; lJR29; lJR30; lJR31; lJR32; lJR34; lJR35; lJR39; lJR40; lJR41; lJR43; lJR45; lJR46.

Restriction analyses demonstrated that 9 different classes were present:

Class 1=lJR3; lJR4; lJR5; lJR15; lJR20; lJR29; lJR34; lJR35.

Class 2=lJR7; lJR8; lJR10; lJR12; lJR19; lJR21; lJR23; lJR26; lJR31; lJR32.

Class 3=lJR11; lJR1; lJR2; lJR6; lJR14; lJR22; lJR25.

Class 4=lJR24; lJR16.

Class 5=lJR27; lJR46.

Class 6=lJR30.

Class 7=lJR39.

Class 8=lJR40; lJR45.

Class 9=lJR43; lJR41.

Clones corresponding to these classes were subcloned into plasmid vector pKS as follows:

Clone lJR3: Xba 1 fragment of 4.0 kb giving pJGR3.2

Clone lJR7: Eco R1 fragment of 2.5 kb giving pJGR7.1

Clone lJR11: Eco R1 fragment of 3.0 kb giving pJGR11.7

Clone lJR24: Cla 1 fragment of 5.0 kb giving pJGR24.10

Clone lJR27: Eco R1 fragment of 2.5 kb giving pJGR27.11

Clone lJR30: Cla 1 fragment of 5.0 kb giving pJGR30.1

Clone lJR39: Cla 1 fragment of 5.0 kb giving pJGR39.27

Clone lJR40; Eco R1 fragment of 3.0 kb giving pJGR40.1

Clone lJR43: Cla 1 fragment of 4.0 kb giving pJGR43.5

Sequence analysis with reverse and forward primers showed that using exact sequence conservation at the nucleotide level, 5 classes were present. These are as follows:

pJGR3.2 pJGR11.7=pJGR40.1 pJGR24.10=pJGR30.1=pJGR39.27 pJGR27.11=pJGR7.1 pJGR43.5

The following subclones were subjected to further sequence analysis.

pJGR3.2 4.0 kb subclone in the Xba 1 site of pKS.

pJGR11.7 3.0 kb subclone in the Eco R1 site of pKS.

pJGR24.10 5.0 kb subclone in the Cla 1 site of pKS.

pJGR27.11 2.5 kb subclone in the Eco R1 site of pKS.

pJGR43.5 4.0 kb subclone in the Cla 1 site of pKS.

The host strain for these subclones was XL1 blue.

Both pJGR3.2 and pJGR24.10 show identical sequence. They also show identical sequence with the leaf cDNA pJRL 6.2.

None of the subclones shows identical sequence with the rape seed cDNA pJRS10.1.

pJGR 43.5 showed sequence which did not correspond to a β-ketoreductase gene.

Further studies concentrated on comparisons of the subclones pJGR11.7 and pJGR27.11. (Partial sequencing only of these subclones has been performed. FIG. 4 shows a theoretical map corresponding to these subclones showing the positions at Box A and Box B. The sequences obtained for pJGR 11.7 for 5' region, Box A and Box B are SEQ.ID-3, SEQ.ID-4 and SEQ.ID-5 respectively. The corresponding sequence for pJGR27.11 are SEQ.ID-6, SEQ.ID-7 and SEQ.ID-8. These subclones showed sequence differences in the 5' translated region, and in the 3' untranslated region.

Single strand confirmation polymorphisms showed that the expression of one of these genes was markedly enhanced in the seed compared with the leaf.

Further studies using RNase protection and "Quantitative competitive PCR" confirmed that the expression of one of these clones was higher in seed than in leaf.

pJGR27.11 contained 0.5 kb of 5' untranscribed information.

pJGR11.7 contained 1.0 kb of 5' untranscribed information.

This region of the gene was isolated from clone pJGR11.7 and cloned into a vector containing a GUS reporter gene. This 11.7 promoter/GUS construct was transformed into rape plants. Expression of GUS activity in the resulting transformants showed that the promoter of the gene corresponding to clone pJGR11.7 is more active in the seed than in the leaf.

Thereafter pJGR 27.11 is cloned into a vector containing the GUS reporter gene and transformed into rape with similar results.

References:

Logemann, J. et al. (1987) Anal. Biochem. 163, 16–20.
Sambrook, J. (1989) "Molecular Cloning: A Laboratory Manual." 2nd Edition. CSH Laboratory Press.
Slabas A. R. et al (1992) Biochem. J. 283, 321–326.

---

We claim:

1. A cDNA of rape seed β-ketoreductase comprising SEQ ID NO:1.

2. A cDNA of rape leaf β-ketoreductase comprising SEQ ID NO:2.

3. A genomic DNA of rape β-ketoreductase pJGR11.7, deposited in *Escherichia coli* strain XL1-Blue with the National Collection of Industrial and Marine Bacteria Limited, 23 St.Machar Drive, Aberdeen AB2 1RY, under the terms of the Budapest Treaty on the Deposit of Microorganism for Patent Purposes, Accession Number 40640, date of deposit May 26, 1994.

4. A genomic DNA of rape β-ketoreductase pJGR24.10, deposited in *Escherichia coli* strain XL1-Blue with the National Collection of Industrial and Marine Bacteria Limited, 23 St.Machar Drive, Aberdeen AB2 1RY, under the terms of the Budapest Treaty on the Deposit of Microorganism for Patent Purposes, Accession Number 40641, date of deposit May 26, 1994.

5. A genomic DNA of rape β-ketoreductase pJGR27.11, deposited in *Escherichia coli* strain XL1-Blue with the National Collection of Industrial and Marine Bacteria Limited, 23 St.Machar Drive, Aberdeen AB2 1RY, under the terms of the Budapest Treaty on the Deposit of Microorganism for Patent Purposes, Accession Number 40642, date of deposit May 26, 1994.

6. An isolated DNA comprising the sequence shown from nucleotide 70 to nucleotide 1014 in SEQ ID NO:1 or the sequence shown from nucleotide 13 to nucleotide 957 in SEQ ID NO:2.

7. A plant transformed with a DNA construct comprising: the sequence shown from nucleotide 70 to nucleotide 1014 in SEQ ID NO:1; or the sequence shown from nucleotide 13 to nucleotide 957 in SEQ ID NO:2.

8. A recombinant vector comprising the sequence shown from nucleotide 70 to nucleotide 1014 in SEQ ID NO:1 or the sequence shown from nucleotide 13 to nucleotide 957 in SEQ ID NO:2.

* * * * *